US00PP19419P2

(12) United States Plant Patent
Jepsen

(10) Patent No.: US PP19,419 P2
(45) Date of Patent: Nov. 4, 2008

(54) ***KALANCHOE* PLANT NAMED 'VICTORIA'**

(50) Latin Name: *Kalanchoe blossfeldiana*
Varietal Denomination: Victoria

(75) Inventor: Knud Jepsen, Hinnerup (DK)

(73) Assignee: Knud Jepsen A/S, Hinnerup (DK)

( * ) Notice: Subject to any disclaimer, the term of this patent is extended or adjusted under 35 U.S.C. 154(b) by 20 days.

(21) Appl. No.: 11/633,113

(22) Filed: Dec. 1, 2006

(51) Int. Cl.
*A01H 5/00* (2006.01)

(52) U.S. Cl. ..... Plt./337; Plt./335
(58) Field of Classification Search ..... Plt./337, Plt./335
See application file for complete search history.

(56) References Cited

PUBLICATIONS

UPOV–ROM GTITM, Plant Variety Database, Feb. 2007, GTI Jouve Retrieval Software, citation for 'Victoria'(2 pages total).*

* cited by examiner

*Primary Examiner*—Anne Marie Grunberg
*Assistant Examiner*—Louanne C Krawcewicz
(74) *Attorney, Agent, or Firm*—C. A. Whealy

(57) ABSTRACT

A new and distinct cultivar of *Kalanchoe* plant named 'Victoria', characterized by its upright, uniform and moderately vigorous growth habit; dark green-colored leaves; uniform, freely and early flowering habit; large red purple-colored flowers; and excellent postproduction longevity.

1 Drawing Sheet

Botanical designation: *Kalanchoe blossfeldiana.*
Cultivar denomination: 'Victoria'.

BACKGROUND OF THE INVENTION

The present invention relates to a new and distinct cultivar of *Kalanchoe,* botanically known as *Kalanchoe blossfeldiana,* and hereinafter referred to by the name 'Victoria'.

The new *Kalanchoe* is a product of a planned breeding program conducted by the Inventor in Hinnenrup, Denmark. The objective of the breeding program is to create new *Kalanchoe* cultivars with attractive foliage and flower coloration.

The new *Kalanchoe* originated from a cross-pollination made by the Inventor in Hinnerup, Denmark in April, 2002, of a proprietary selection of *Kalanchoe blossfeldiana* identified as code number 1999-673, not patented, as the female, or seed parent with the *Kalanchoe blossfeldiana* cultivar Purple Jaqueline, described in U.S. Plant Pat. No. 12,310, as the male, or pollen, parent. The cultivar Victoria was discovered and selected by the Inventor as a flowering plant from within the progeny of the stated cross-pollination in a controlled environment in Hinnerup, Denmark in March, 2003.

Asexual reproduction of the new *Kalanchoe* by vegetative terminal cuttings in a controlled environment in Hinnerup, Denmark since June, 2003, has shown that the unique features of this new *Kalanchoe* are stable and reproduced true to type in successive generations.

SUMMARY OF THE INVENTION

The cultivar Victoria has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Victoria'. These characteristics in combination distinguish 'Victoria' as a new and distinct cultivar of *Kalanchoe:*

1. Upright, uniform and moderately vigorous growth habit.
2. Dark green-colored leaves.
3. Uniform, freely and early flowering habit.
4. Large red purple-colored flowers.
5. Excellent postproduction longevity.

Plants of the new *Kalanchoe* can be compared to plants of the female parent selection. Plants of the new *Kalanchoe* differ primarily from plants of the female parent selection primarily in plant size and flower color.

Plants of the new *Kalanchoe* can also be compared to plants of the male parent, the cultivar Purple Jaqueline. Plants of the new *Kalanchoe* differ from plants of the cultivar Purple Jaqueline in the following characteristics:

1. Plants of the new *Kalanchoe* have smaller flowers than plants of the cultivar Purple Jaqueline.
2. Plants of the new *Kalanchoe* and the cultivar Purple Jaqueline differ in flower color.
3. Plants of the new *Kalanchoe* flower about five days later than plants of the cultivar Purple Jaqueline.

Plants of the new *Kalanchoe* can be compared to plants of the *Kalanchoe blossfeldiana* cultivar Ann, not patented. In side-by-side comparisons conducted in Hinnerup, Denmark, plants of the new *Kalanchoe* differed from plants of the cultivar Ann in the following characteristics:

1. Plants of the new *Kalanchoe* were more compact than plants of the cultivar Ann.
2. Leaves of plants of the new *Kalanchoe* were more serrated than leaves of plants of the cultivar Ann.
3. Plants of the new *Kalanchoe* had smaller flowers than plants of the cultivar Ann.

4. Plants of the new *Kalanchoe* and the cultivar Ann differed in flower color.

5. Plants of the new *Kalanchoe* flowered about four days later than plants of the cultivar Ann.

BRIEF DESCRIPTION OF THE PHOTOGRAPHS

The accompanying colored photographs illustrate the overall appearance of the new *Kalanchoe,* showing the colors as true as it is reasonably possible to obtain in colored reproductions of this type. Colors in the photographs may differ slightly from the color values cited in the detailed botanical description which accurately describe the colors of the new *Kalanchoe.*

The photograph at the top of the sheet comprises a side perspective view of a typical flowering plant of 'Victoria' grown in a container.

The photograph at the bottom of the sheet comprises a top perspective view of a typical flowering plant of 'Victoria' grown in a container.

DETAILED BOTANICAL DESCRIPTION

The aforementioned photographs and following observations, measurements and values describe plants grown in Hinnerup, Denmark in a glass-covered greenhouse during the summer and under conditions which closely approximate commercial production. During the production of the plants, day temperatures were about 19° C., night temperatures were about 21° C. and light levels ranged from 10 kilolux to 50 kilolux. Unrooted cuttings were directly stuck in 10-cm containers and received long day/short night conditions (more than 14 hours of light) for about two weeks; plants then received photoinductive short day/long night conditions (minimum 14 hours darkness) until flowering. Plants were about 15 weeks old when the photographs and the description were taken. In the detailed description, color references are made to The Royal Horticultural Society Colour Chart, 2001 Edition, except where general terms of ordinary dictionary significance are used.

Botanical classification: *Kalanchoe blossfeldiana* cultivar Victoria.

Parentage:

*Female, or seed, parent.*—Proprietary selection of *Kalanchoe blossfeldiana* identified as code number 1999-673, not patented.

*Male or pollen parent.*—*Kalanchoe blossfeldiana* cultivar Purple Jaqueline, disclosed in U.S. Plant Pat. No. 12,310.

Propagation:

*Type.*—By vegetative terminal cuttings.

*Time to initiate roots, summer.*—About two weeks at temperatures of 19° C. to 21° C.

*Time to initiate roots, winter.*—About three weeks at temperatures of 19° C. to 21° C.

*Time to produce a rooted young plant, summer.*—About 21 days at temperatures of 19° C. to 21° C.

*Time to produce a rooted young plant, winter.*—About 24 days at temperatures of 19° C. to 21° C.

*Root description.*—Fine, fibrous; white in color.

*Rooting habit.*—Freely branching; moderately dense.

Plant description:

*Plant habit.*—Upright, uniform and moderately vigorous growth habit. Very freely flowering with numerous compound cymes. Inverted triangle with rounded crown. Appropriate for 9-cm to 10-cm containers.

*Plant height at flowering.*—About 25 cm.

*Plant diameter at flowering.*—About 20 cm.

*Branching habit.*—Usually about three to six lateral branches develop per plant. Pinching (removal of the terminal apex) is not required but will enhance lateral branch development.

Lateral branch description:

*Length.*—About 8 cm to 12 cm.

*Diameter.*—About 4 mm.

*Internode length.*—About 2 cm to 6 cm.

*Aspect.*—Erect.

*Strength.*—Strong.

*Texture.*—Smooth, glabrous.

*Color.*—147B.

Foliage description:

*Arrangement.*—Opposite, simple; generally symmetrical.

*Length, vegetative plants.*—About 8 cm to 11 cm.

*Width, vegetative plants.*—About 5 cm to 7 cm.

*Length, generative plants.*—About 5 cm to 7 cm.

*Width, generative plants.*—About 2 cm to 4 cm.

*Shape.*—Ovate.

*Apex.*—Rounded.

*Base.*—Rounded.

*Margin.*—Serrate.

*Texture, upper and lower surfaces.*—Glabrous, leathery; succulent.

*Venation pattern.*—Pinnate.

*Color.*—Developing and fully expanded foliage, upper surface: 147A; venation, 147A. Developing and fully expanded foliage, lower surface: 147B; venation, 147B.

*Petiole.*—Length: About 1 cm to 1.5 cm. Diameter: About 5 mm to 7 mm. Texture, upper and lower surfaces: Smooth, glabrous. Color, upper surface: 137D. Color, lower surface: 137C.

Flower description:

*Flower arrangement and habit.*—Single flowers arranged singly in compound dichasial cymes that arise from leaf axils. Uniform and freely flowering habit with usually about 55 to 65 flowers per inflorescence. Flowers not persistent. Flowers not fragrant.

*Natural flowering season.*—Plants of the new *Kalanchoe* initiate and develop flowers under short day/long night conditions or during late summer autumn/winter/early spring. Flower initiation and development can also be induced under artificial short day/long night conditions (at least 14 hours of darkness).

*Time to flower.*—Early flowering habit; under short day/long night photoinductive conditions, about 71 days are required. Actual time to flower is primarily dependent upon temperature and light intensity.

*Post-production longevity.*—Excellent post-production longevity; plants maintain good foliage and flower substance for about six weeks under interior environmental conditions.

*Inflorescence height.*—About 8 cm to 12 cm.

*Inflorescence diameter.*—About 6 cm.

*Flower diameter.*—About 2 cm.

*Flower length (height).*—About 1 cm.

*Flower bud.*—Shape: Lanceolate to ovate. Length: About 1.2 cm. Diameter: About 3 mm. Color: 64A.

*Petals.*—Arrangement: About four fused at the base. Length (largest petals): About 7 mm. Width (largest petals): About 7 mm. Aspect: Slightly upright to eventually recurved. Shape: Ovate. Apex: Mucronate. Margin: Entire. Texture, upper and lower surfaces: Smooth, glabrous. Color: When opening, upper surface: 60A. When opening, lower surface: 71C and 70C. Fully opened, upper surface: 71B. Fully opened, lower surface: 71C and 70C.

*Sepals.*—Appearance: Four fused at the base. Length: About 6 mm. Width: About 2 mm. Shape: Lanceolate. Apex: Acute. Margin: Entire. Texture, upper and lower surfaces: Smooth; glabrous. Color, immature, upper and lower surfaces: 146A. Color, mature, upper and lower surfaces: 146A.

*Peduncles.*—Length: About 5 mm to 2 cm. Diameter: About 1 mm. Aspect: Erect to perpendicular. Strength: Strong. Texture: Smooth, glabrous. Color: 137C.

*Reproductive organs.*—Androecium: Stamen number: About five to ten per flower. Anther shape: Elliptic, flat. Anther size: About 1 mm by 1 mm. Anther color: Close to 22A. Amount of pollen: Abundant. Pollen color: Close to 20A. Gynoecium: Pistil number: About four per flower. Pistil length: About 3 mm. Style length: About 2 mm. Style color: 145A. Stigma shape: Rounded. Stigma color: 145A. Ovary color: Close to 138A.

*Seed.*—Quantity of seeds per ovary: Numerous. Length: Less than 1 mm. Diameter: Less than 1 mm. Color: 145C.

Temperature tolerance: Plants of the new *Kalanchoe* have been observed to tolerate temperatures from about 5° C. to about 30° C.

Pathogen/pest resistance: Plants of the new *Kalanchoe* have not been observed to be resistant to pests and pathogens common to *Kalanchoes*.

It is claimed:

1. A new and distinct *Kalanchoe* plant named 'Victoria' as illustrated and described.

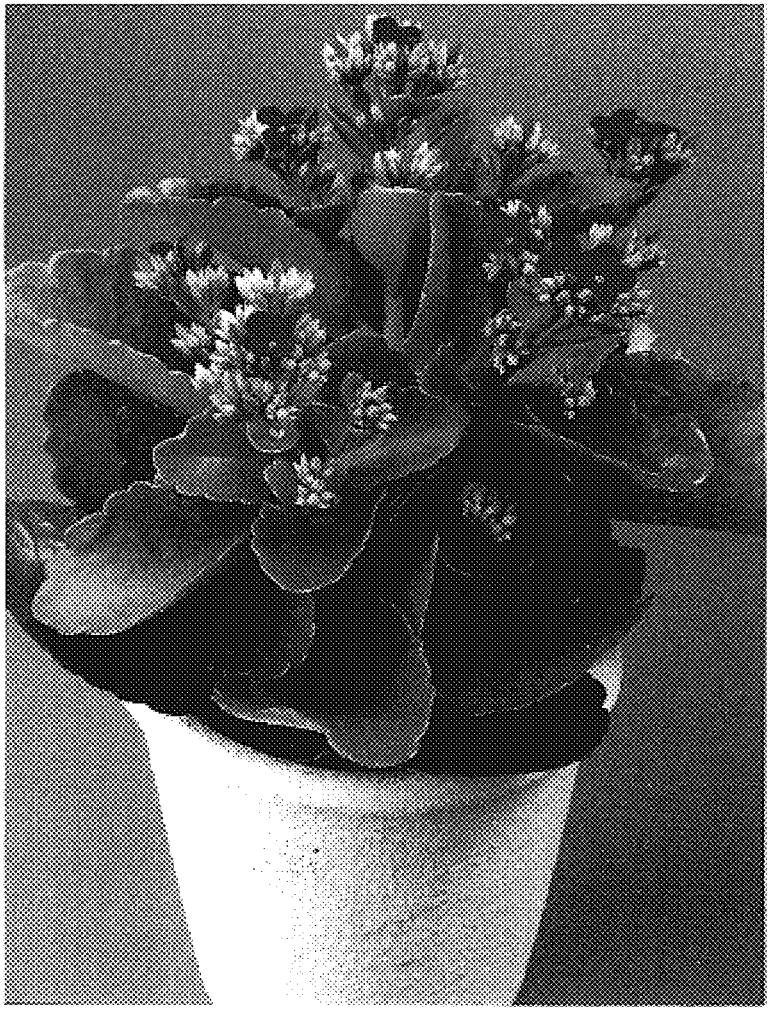
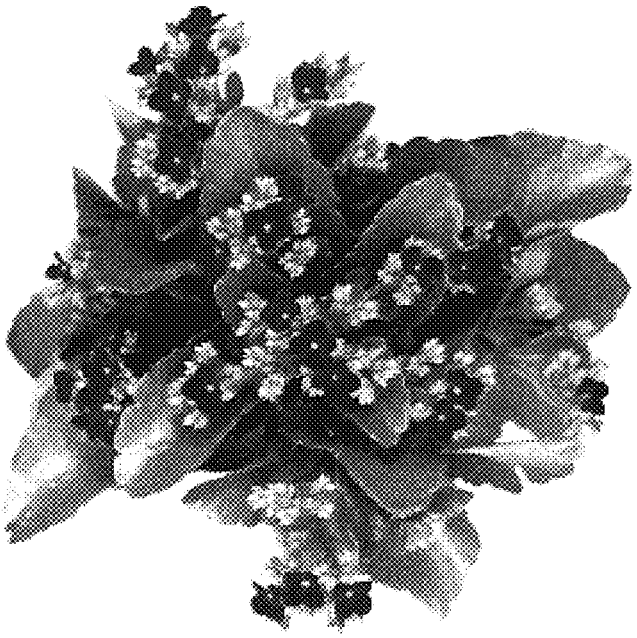

* * * * *